(12) United States Patent
Carbone et al.

(10) Patent No.: US 10,054,321 B2
(45) Date of Patent: Aug. 21, 2018

(54) AIR CLEANING APPARATUS AND METHOD FOR CONTAINER

(71) Applicants: Philip C. Carbone, North Reading, MA (US); Karen Benedek, Winchester, MA (US); Peter J. Loftus, Cambridge, MA (US)

(72) Inventors: Philip C. Carbone, North Reading, MA (US); Karen Benedek, Winchester, MA (US); Peter J. Loftus, Cambridge, MA (US)

(73) Assignee: BLUEZONE IP HOLDING LLC, Woburn, MA (US)

( * ) Notice: Subject to any disclaimer, the term of this patent is extended or adjusted under 35 U.S.C. 154(b) by 36 days.

(21) Appl. No.: 15/065,446

(22) Filed: Mar. 9, 2016

(65) Prior Publication Data

US 2016/0265796 A1 Sep. 15, 2016

Related U.S. Application Data

(60) Provisional application No. 62/130,381, filed on Mar. 9, 2015.

(51) Int. Cl.
*B01D 46/10* (2006.01)
*F24F 3/16* (2006.01)
*A61L 9/00* (2006.01)

(52) U.S. Cl.
CPC .................. *F24F 3/16* (2013.01); *A61L 9/00* (2013.01); *F24F 2003/1667* (2013.01); *F24F 2003/1685* (2013.01)

(58) Field of Classification Search
CPC ............ B01D 46/0023; B01D 46/0028; B01D 46/10; B01D 2275/305; F25D 17/042; F25D 2317/0417; F25D 2317/0416; F24F 2003/1667
USPC ...... 55/385.3, 471, 487, 473, 385.1; 96/224, 96/226; 62/78, 440; 422/121, 291
See application file for complete search history.

(56) References Cited

U.S. PATENT DOCUMENTS

| | | | |
|---|---|---|---|
| 5,755,103 A | 5/1998 | Na et al. | |
| 6,004,365 A * | 12/1999 | Fiacco | B01D 45/14 55/400 |
| 6,092,430 A * | 7/2000 | Liston | A23L 3/3418 422/3 |
| 6,156,085 A * | 12/2000 | Chiu | B01D 46/24 55/357 |

(Continued)

FOREIGN PATENT DOCUMENTS

| | | |
|---|---|---|
| CN | 101190338 A | 6/2008 |
| JP | 2000217898 A | 8/2000 |
| WO | WO 1997/034682 A1 | 9/1997 |

*Primary Examiner* — Amber R Orlando
*Assistant Examiner* — Minh-Chau Pham
(74) *Attorney, Agent, or Firm* — Pauley Erickson & Kottis

(57) ABSTRACT

An apparatus and method for cleaning contaminated air in an enclosed space, such as a transportation trailer or a shipping container. An air mover in the space circulates contaminated atmosphere from an area of low pressure to an area of higher pressure. The resulting pressure differential is used to draw a reverse, partial air flow through an air cleaning device. The repeated cycling of a portion of airflow results in cleaning of the atmosphere and a general reduction of the contaminant from the enclosed space.

20 Claims, 3 Drawing Sheets

(56) References Cited

U.S. PATENT DOCUMENTS

| | | | | |
|---|---|---|---|---|
| 6,156,088 | A | * | 12/2000 | Cardarelli ............ A24F 19/0042 131/231 |
| 6,286,330 | B1 | * | 9/2001 | Kopf ..................... F25D 17/042 62/314 |
| 6,454,841 | B1 | * | 9/2002 | Kaiser ................ B01D 46/0023 55/385.1 |
| 6,494,940 | B1 | | 12/2002 | Hak |
| 6,606,869 | B2 | * | 8/2003 | Takahashi ............. F25D 17/042 62/131 |
| 6,736,885 | B2 | * | 5/2004 | Kaiser ................ B01D 46/0023 55/385.3 |
| 6,979,359 | B2 | | 12/2005 | Laiti |
| 8,114,358 | B2 | | 2/2012 | Benedek et al. |
| 8,388,900 | B2 | | 3/2013 | Benedek et al. |
| 2008/0118395 | A1 | | 5/2008 | Benedek |
| 2012/0244036 | A1 | | 9/2012 | Benedek et al. |
| 2013/0287626 | A1 | | 10/2013 | Benedek et al. |
| 2015/0375602 | A1 | * | 12/2015 | Fields ..................... B60H 3/06 55/385.3 |

\* cited by examiner

AIR CLEANING APPARATUS AND METHOD FOR CONTAINER

CROSS REFERENCE TO RELATED APPLICATION(S)

This application claims the benefit of U.S. Provisional Patent Application Ser. No. 62/130,381, filed on 9 Mar. 2015. The Provisional Patent Application is hereby incorporated by reference herein in its entirety and is made a part hereof, including but not limited to those portions which specifically appear hereinafter.

FIELD OF THE INVENTION

This invention relates generally to air cleaning of enclosures, and, more particularly, to an apparatus and method for energy efficient air cleaning of sealed enclosures, such as refrigerated shipping containers or trucks.

BACKGROUND OF THE INVENTION

Perishable goods are shipped in refrigerated containers in order to maintain freshness and quality. Refrigerated containers can keep pallets of perishable goods cold by establishing a circulation of air from the container, for example, through a refrigeration unit and back into the container. The refrigeration unit can include or have a standard vapor compression cycle, with an evaporator cooling the air and a condenser rejecting heat to the outside of the container.

Perishable goods, like fruits and vegetables, respire during storage or transport in the refrigerated container. The fruits and vegetables convert oxygen to carbon dioxide as they respire. They also give off or emit other gases, such as ethylene or volatile compounds, such as aldehydes or alcohols or other hydrocarbons, which have characteristic odors and/or can impact ripening. These gases, such as carbon dioxide and ethylene, can build up or increase in volumes and/or quantities in shipping containers. In addition, microbes such as molds or fungus can grow in a container filled with perishable goods. The microbes reproduce by producing relatively high volumes of spores that are transported through the air to new surfaces. Relatively high concentrations of spores in the air have been shown to lead to relatively high concentrations of spores on the surfaces of perishable items.

It is possible to vent the gases and spores by allowing some air in the container to exhaust from the container while pulling in air from outside the container to replace it. Ventilation procedures are well established in the storage and shipping business to lower levels of carbon dioxide and ethylene in the containers.

Ventilation can result in additional energy usage to condition the outside air that is introduced into the container. In addition, the outside air may not be completely clean. It contains humidity, fumes from outside sources of contaminants, and the exhaust gases of nearby containers. Some of these contaminants are not desirable in the refrigerated container. Relatively high ventilation rates can increase the operation of the evaporator, which, in turn, can dry out the air in the container and lead to moisture loss from the perishables.

There is a continuing need for improved air cleaning in storage containers, such as with a reduction or elimination of air venting to save on cooling energy and cost.

SUMMARY OF THE INVENTION

The invention provides an apparatus and method for cleaning the air of contaminants in an enclosed space in addition to or instead of ventilating the enclosure to clean the air. The invention is suitable for any enclosed space, such as, without limitation, a transportation trailer, a storage trailer, a storage bin, a bag, a shipping container, an equipment bin or an expandable structure. The invention can be retrofitted or otherwise added to or with existing air movers (e.g., refrigeration unit blowers) or integrated in or with newly constructed air mover devices.

The general object of the invention can be attained, at least in part, through an atmosphere treatment assembly for at least one of sanitizing, decontaminating, deodorizing, conditioning or drying an atmosphere within an enclosed space and exposed to a contaminant. The assembly can beneficially be incorporated with either a new or existing air mover, such as a fan already in an existing refrigeration unit. The air mover has a first side and an opposite second side, and circulates contaminated atmosphere from the enclosed space in a first direction from the first side to the second side. The assembly includes an atmosphere treating unit, such as an air cleaning device, in combination with the air mover. A portion of the contaminated atmosphere on the second side of the air mover circulates through the atmosphere treating unit in a second direction opposite the first direction and back to the first side of the air mover.

The portion of the contaminated atmosphere on the second side of the air mover circulates through the atmosphere treating unit as a result of a pressure differential between the first side and the second side, and without a reverse air mover, such as a separate, reverse direction fan. The repeated cycling of the portion of airflow results in cleaning of the atmosphere and a general reduction and/or elimination of the contaminant from the air flow and/or the atmosphere within the enclosed space. Exemplary contaminants removable by the apparatus and method of this invention include, without limitation, ethylene, odors, bacteria, spores, microorganisms or volatile matter.

The invention further includes an atmosphere treatment assembly including an air mover with a fan adapted to move a flow of contaminated atmosphere from a region of low pressure to a region of high pressure. An atmosphere treating unit connects the region of high pressure to the region of low pressure, and a portion of the contaminated atmosphere in the high pressure region circulates through the atmosphere treating unit back to the region of low pressure as a function of a pressure differential between the region of low pressure and the region of high pressure.

The invention further includes a method for at least one of sanitizing, decontaminating, deodorizing, conditioning or drying an atmosphere exposed to a contaminant within a space. The method includes circulating a flow of the atmosphere containing the contaminant via an air mover from an air mover first side to an air mover second side. The air mover creates a pressure differential between the first side and the second side, such that a portion of the flow then passes through an atmosphere treating unit as a function of the created pressure differential. The portion of the flow passing through the atmosphere treatment unit has a reverse flow back to the first side of the air mover as a function of the pressure differential between the opposing sides.

In embodiments of this invention, it is cost effective and more reliable for a device or apparatus to operate without its own air moving device, such as a fan. It is desirable for the air flow established by the refrigeration unit itself to drive flow through the atmosphere treating unit. In good practice, the air flow through the atmosphere treating unit is established so that it creates an air exchange of the entire

DESCRIPTION OF ILLUSTRATED EMBODIMENTS

Figure 1:
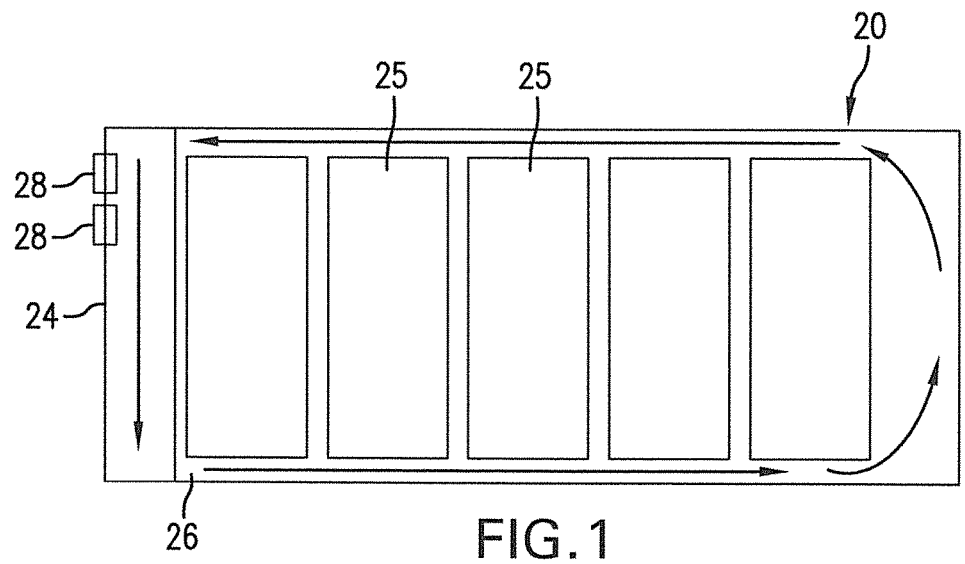
FIG. 1 illustrates a direction of air flow in a refrigerated container that is filled or at least partially filled with pallets of perishable goods.

FIG. 1 shows one possible direction of air flow in a refrigerated container 20 that is filled or at least partially filled with pallets 25 of perishable goods. In FIG. 1, air flows downward through the refrigeration unit 24 and is directed into a hollow or slatted floor 26 and/or other similar surface or venting of the container 20. In the embodiment shown in FIG. 1, the air flows through a "T-Floor" to the opposite end of the container 20. The air flows upward and across the top of the container 20, above the pallets 25, and then is sucked or drawn into the top of the refrigeration unit 24. Openings 28 can be used for ventilation into and out of the container 20 are used to reduce or remove contaminants, and can be located in the refrigeration unit 24 or elsewhere in the container 20. This invention can be used as an alternative to, or in concert with, known or other suitable ventilation openings or systems.

Figure 2:
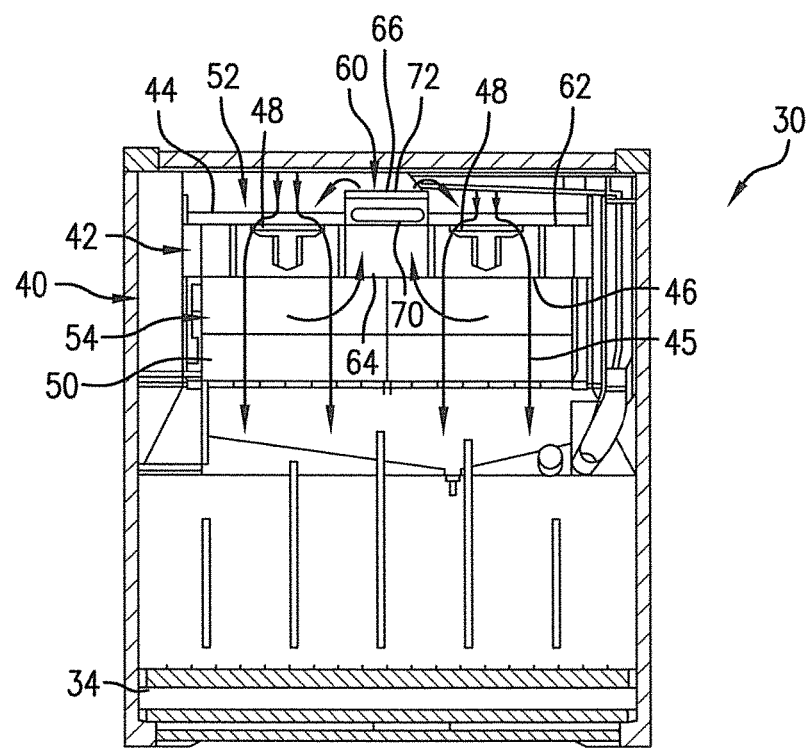
FIG. 2 is a sectional view of a container refrigeration unit, according to one embodiment of this invention.

FIG. 2 shows a front view of container 30 with a refrigeration unit 40, according to some embodiments of this invention. The refrigeration unit 40 is connected to a storage enclosure of the container 30. The refrigeration unit 40 includes an air mover 42, having a first side 44 and an opposite second side 46. The air mover of embodiments of this invention includes at least one fan, and in FIG. 2 is shown with two side-by side fans 48. As illustrated by the direction arrows 45, the fans 48 can draw or pull the air from the top of the refrigeration unit 40, and blow or force the air to and thorough or over an evaporator 50 where the air is cooled, and then down to the floor 34 of the container 30. The use of the fans 48 establishes a region of low pressure 52 at the first side 44 of the air mover 42 and a region of high pressure 54 at the second side that is relatively higher than the low pressure region 52.

In some embodiments of this invention, the direction of flow illustrated in FIG. 2 is from the top of the refrigeration unit 40 to the bottom. However, in other embodiments of this invention, the entire system can operate in other suitable flow patterns, such as in reverse and flow from bottom to top and circulate through the container 30 in the opposite flow direction.

The air flow through the refrigeration unit 40 includes contaminants from the container 30, such as off-gases and/or mold spores from stored produce. The invention includes an atmosphere treating unit for removing contaminants from the air flow through the refrigeration unit. FIG. 2 illustrates an atmosphere treating unit 60, mounted to a transom 62 or other suitable structure between the two fans 48.

Arrows in FIG. 2 illustrate the direction of flow through an inlet 64 of the atmosphere treating unit 60, at or adjacent to the second side high pressure region 54, and out an outlet 66 at or adjacent to the first side low pressure region 52. In some embodiments of this invention, only a portion, such as a relatively small amount, of the air flow travels in the reverse direction of or relative to the bulk or main flow. In some embodiments of this invention, the air flow through the atmosphere treating unit 60 is pushed, pulled, or otherwise moved from the relatively high pressure region 54 downstream of the air mover 42 and above the evaporator 50 to the relatively low pressure region 52 at the inlet first side 44 of the fans 48. Air is cleaned in the atmosphere treating unit 60. Clean air is then mixed into the main air flow, for example, in the fans 48 and is blown across the evaporator 50 and back into the container 30.

In this way, according to some embodiments of this invention, the atmosphere treating unit 60 or other air cleaner can operate without an independent, powered air moving device, such as a fan or blower. The partial reverse flow can be considered a passive flow, without a separate air mover creating an active flow. The air flow of or through the container 30 and/or refrigeration unit 40 drives or creates a pressure differential that establishes a partial reverse flow through a passage of the atmosphere treating unit 60. In some embodiments of this invention, the partial reverse flow eventually mixes back with the bulk or main air flow. In some embodiments of this invention, over a time period, the air in the container 30 is completely cleaned or almost completely cleaned. The rate of air flow through the atmosphere treating unit 60 can be controlled by the size and location of inlet and/or outlet openings in the atmosphere treating unit 60.

Figure 3:
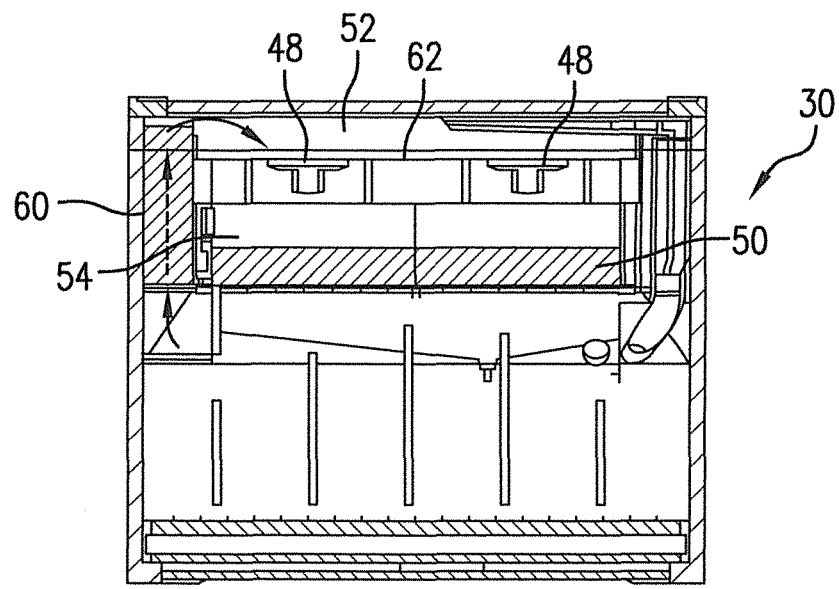
FIG. 3 is a sectional view of a container refrigeration unit, according to another embodiment of this invention.

Various and alternative sizes, shapes, placements, types, numbers, and/or configurations are available for the air mover and the atmosphere treating unit of this invention, or any component thereof. As an example, FIG. 3 illustrates an alternative atmosphere treatment assembly, having an alternative atmosphere treating unit 60 location, according to one embodiment of this invention, that still allows a flow through the atmosphere treating unit 60 or other air cleaner that is in the reverse direction, for example, relative to the bulk or main flow of or through the refrigeration unit 40. The atmosphere treating unit 60 is disposed to one side, and optionally two or more sides, of the air mover 42. The atmosphere treating unit 60 extends along a side of the air mover 42 and connects the second side high pressure region 54 to the first side low pressure region 52.

Figure 4:
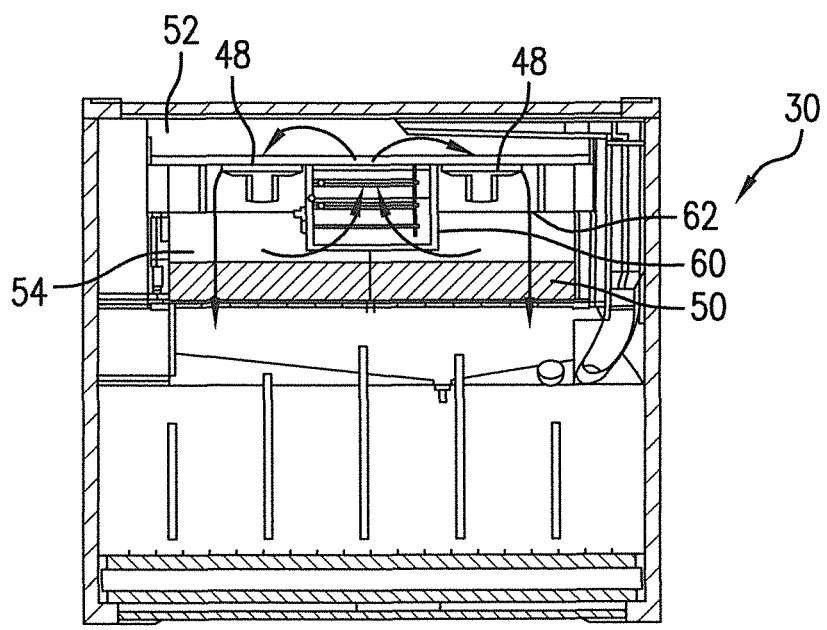
FIG. 4 is a sectional view of a container refrigeration unit, according to yet another embodiment of this invention.

FIG. 4 shows yet a further alternative configuration of the atmosphere treating unit 60, according to some embodiments of this invention. In FIG. 4, the atmosphere treating unit 60 is or extends below the transom 62 between the two evaporator fans 48.

The atmosphere treating unit of this invention can be or include any one or more suitable filters or contaminant removal devices. In some embodiments of this invention, the atmosphere treating unit can be one that is intended primarily to clean ethylene and/or mold out of or from the air with the use of UV light and/or ozone. In one exemplary configuration, air flows into the atmosphere treating unit 60 where it is mixed with ozone that is generated from the UV lights, such as lights 70 positioned perpendicularly to atmosphere flow through the atmosphere treating unit 60. Ethylene and other hydrocarbons can be oxidized by the ozone in the presence of the UV light. Mold spores can be killed by the UV light and ozone. The air can be exhausted from the atmosphere treating unit 60 or other air cleaner through a catalyst 72 that removes any remaining ozone from the air. In some embodiments of this invention, the catalyst is an oxidizing catalyst that further oxidizes any hydrocarbons that are not completely reacted by the ozone.

Exemplary UV cleaning devices suitable for use as, including any suitable modification, the atmosphere treating unit include air cleaners disclosed in, for example: U.S. patent application Ser. No. 13/784,503, published as U.S. Publication 2013-0287626; U.S. patent application Ser. No. 13/512,564, published as U.S. Publication 2012-0244036; U.S. Pat. No. 8,388,900; U.S. Pat. No. 8,114,358; and U.S. patent application Ser. No. 11/603,669, published as U.S. Publication 2008-0118395. The entire disclosures of all of these publications are hereby incorporated by reference herein in their entirety and made a part of this specification.

Figure 5:
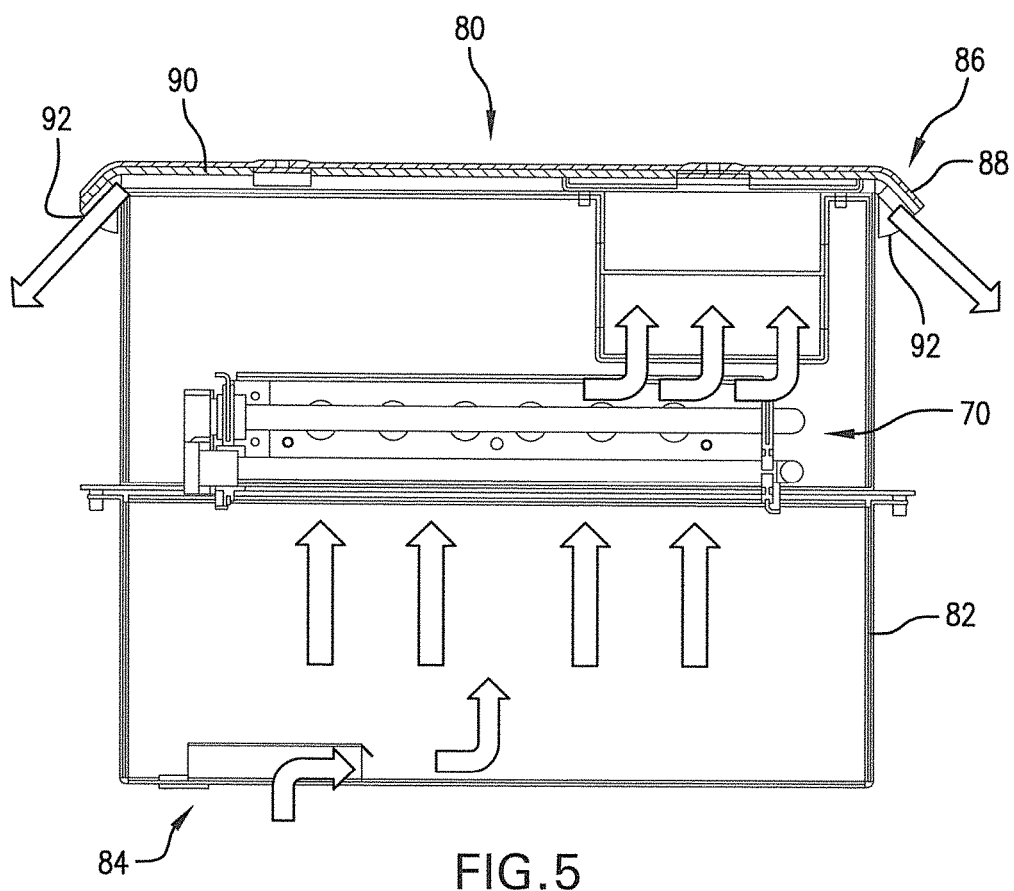
FIG. 5 illustrates an atmosphere treating unit according to one embodiment of this invention.

FIG. 5 illustrates an atmosphere treating unit 80 according to embodiments of this invention. The atmosphere treating unit 80 includes a housing 82 having an air flow inlet 84 and an outlet 86 on an opposite side from the inlet 84. In embodiments of this invention, the air flow rate and/or distribution through the atmosphere treating unit 80 is controlled through the size(s) of the inlet 84 and/or outlet 86. Each of the inlet 84 and outlet 86 shown in FIG. 5 can be adjustable, and can be controlled by any suitable control device and algorithm. The inlet 84 includes an adjustable flow control and distribution baffle to vary the air intake, thus also controlling the rate of airflow within and exiting the atmosphere treating unit 80.

The outlet 86 of FIG. 5 is embodied as an outlet flow control and distribution baffle 88. The outlet flow baffle 88 includes a cover 90 for the atmosphere treating unit 80, which provides one or more outlet openings 92 at or along upper edges, and desirably along opposing sides, of the atmosphere treating unit 80. In embodiments of this invention, such as shown in FIG. 5, the outlet flow baffle 88 includes air outlets 92 angled in a direction downward toward the inlet 84 and/or the air mover, thereby directing exiting air in a direction closer to the general air flow path through the refrigeration unit and/or container. The air outlets 92 are optionally adjustable in size and/or closable. As will be appreciated, various sizes, shapes and configurations are available for the housing, inlet, outlet(s), and baffles of the atmosphere treating unit 80, depending on need. Air treatment devices, such as UV lights 70 and/or catalysts, discussed above can be incorporated in the atmosphere treating unit 80, according to need.

While in the foregoing detailed description this invention has been described in relation to certain preferred embodiments thereof, and many details have been set forth for purposes of illustration, it will be apparent to those skilled in the art that this invention is susceptible to additional embodiments and that certain of the details described herein can be varied considerably without departing from the basic principles of this invention.

What is claimed is:

1. An atmosphere treatment assembly for at least one of sanitizing, decontaminating, deodorizing, conditioning or drying an atmosphere within an enclosed space and exposed to a contaminant, the enclosed space including an air mover with a first side and an opposite second side, wherein the air mover draws contaminated atmosphere at the first side in through an air mover inlet in a first direction and blows the contaminated atmosphere out an air mover outlet at the second side, the assembly comprising:

an atmosphere treating unit in combination with the air mover, the atmosphere treating unit including a unit inlet and a unit outlet, wherein the unit inlet is disposed toward the second side of the air mover and the air mover outlet, and the unit outlet is disposed toward the first side of the air mover adjacent to the air mover inlet, wherein a portion of the contaminated atmosphere that is blown out the air mover outlet enters through the unit inlet of the atmosphere treating unit and circulates in a second direction opposite the first direction through the atmosphere treating unit to provide treated atmosphere out through the unit outlet back into the contaminated atmosphere on the first side of the air mover.

2. The apparatus according to claim 1, wherein the portion of the contaminated atmosphere on the second side of the air mover circulates through the atmosphere treating unit as a function of a pressure differential between the first side and the second side, and without a reverse air mover device.

3. The apparatus according to claim 1, wherein the air mover forms a pressure differential including a low pressure region on the first side and a high pressure region on the second side, and the pressure differential causes the portion of the contaminated atmosphere to circulate through the atmosphere treating unit.

4. The apparatus according to claim 3, wherein the atmosphere treating unit includes an inlet at or adjacent the high pressure region and an outlet at or adjacent the low pressure region.

5. The apparatus according to claim 1, wherein the air mover comprises a fan.

6. The apparatus according to claim 1, wherein the atmosphere treating unit is disposed between two fans of the air mover, wherein each of the two fans draws contaminated atmosphere in the first direction through the first side and blows the contaminated atmosphere out the second side.

7. The apparatus according to claim 1, wherein the atmosphere treating unit extends along a side of the air mover and comprises a passageway separated from the air mover by a passageway wall.

8. The apparatus according to claim 1, wherein the contaminant comprises at least one of ethylene, an odor, a bacteria, a spore, a microorganism, or a volatile matter.

9. The atmosphere treatment assembly according to claim 1, wherein the atmosphere treating unit comprises UV light bulbs used to generate ozone and to irradiate ozone mixed with the contaminated atmosphere and wherein the UV light bulbs are oriented perpendicularly to atmosphere flow through the atmosphere treating unit.

10. The atmosphere treatment assembly according to claim 1, wherein the atmosphere treating unit comprises an inlet baffle and an outlet flow baffle, and an air flow rate and distribution through the atmosphere treating unit is controlled through the inlet baffle and the outlet flow baffle.

11. The atmosphere treatment assembly according to claim 1, wherein the enclosed space is one of a transportation trailer, a storage trailer, a storage bin, a bag, a shipping container, an equipment bin or an expandable structure.

12. An atmosphere treatment assembly for at least one of sanitizing, decontaminating, deodorizing, conditioning or drying an atmosphere within an enclosed space and exposed to a contaminant, the assembly comprising:

an air mover including a first passageway with a fan adapted to move a flow of contaminated atmosphere through the passageway from a region of low pressure to a region of high pressure; and an atmosphere treating unit including a second passageway separated from the first passageway, the second passageway connecting the region of high pressure to the region of low pressure, wherein a portion of the contaminated atmosphere in the high pressure region circulates through the atmosphere treating unit back to the region of low pressure as a function of a pressure differential between the region of low pressure and the region of high pressure.

13. The apparatus according to claim 12, wherein the first passageway includes a first side adjacent the low pressure region and an opposite second side adjacent the high pressure region, the air mover circulates contaminated atmosphere in a direction through the first side and out through second side, and the second passageway extends adjacent and parallel to the first passageway, and includes an inlet at or adjacent the high pressure region and an outlet at or adjacent the low pressure region.

14. The apparatus according to claim 12, wherein the air mover comprises a fan.

15. The apparatus according to claim 12, wherein the atmosphere treating unit is disposed between two fans of the air mover.

16. The apparatus according to claim 12, further comprising an evaporator disposed in or adjacent to the high pressure region, wherein high pressure air of the high pressure region is forced through or blown over the evaporator by the fan.

17. The atmosphere treatment assembly according to claim 12, wherein the atmosphere treating unit comprises UV light bulbs used to generate ozone and to irradiate ozone mixed with the contaminated atmosphere and wherein the UV light bulbs are oriented perpendicularly to atmosphere flow through the atmosphere treating unit.

18. The atmosphere treatment assembly according to claim 12, wherein the enclosed space is one of a transportation trailer, a storage trailer, a storage bin, a bag, a shipping container, an equipment bin or an expandable structure.

19. A method for at least one of sanitizing, decontaminating, deodorizing, conditioning or drying an atmosphere exposed to contaminants within a space, the method comprising:
 circulating a first flow of the atmosphere containing the contaminants via an air mover including a first side and an opposite second side, wherein the atmosphere and the contaminants flow through the air mover from the first side to the second side;
 the air mover creating a pressure differential between the first side and the second side; and
 passing a portion of the first flow and a portion of the contaminants through an atmosphere treating unit as a function of the pressure differential, wherein the portion of the first flow passing through the atmosphere treatment unit comprises a reverse flow opposite the first flow, and the portion of the flow exits the second side of the air mover and passes through the atmosphere treating unit back to the first side of the air mover as a function of the pressure differential to provide treated atmosphere back into the contaminated atmosphere on the first side of the air mover.

20. The apparatus according to claim 3, further comprising an evaporator adjacent to the second side of the air mover, wherein the contaminated atmosphere is blown over the evaporator by the fan.

* * * * *